United States Patent [19]

Bates

[11] Patent Number: 6,167,107
[45] Date of Patent: Dec. 26, 2000

[54] AIR PUMP FOR PARTICLE SENSING USING REGENERATIVE FAN, AND ASSOCIATED METHODS

[75] Inventor: Thomas Bates, Westminster, Colo.

[73] Assignee: Particle Measuring Systems, Inc., Boulder, Colo.

[21] Appl. No.: 09/356,232

[22] Filed: Jul. 16, 1999

[51] Int. Cl.[7] .................................................. G06M 11/02
[52] U.S. Cl. ............................................................. 377/10
[58] Field of Search ................................................. 377/10

[56] References Cited

U.S. PATENT DOCUMENTS

| 5,515,164 | 5/1996 | Kreikebaum et al. . | |
|---|---|---|---|
| 5,600,438 | 2/1997 | Kreikebaum et al. . | |
| 5,825,487 | 10/1998 | Felbinger et al. . | |
| 5,887,439 | 12/1999 | Kotliar | 62/78 |
| 6,003,389 | 12/1999 | Flagan et al. | 73/865.5 |

OTHER PUBLICATIONS

Ametek Rotron TMD Industrial Products, "A Variable Flow Blower Product Specifications Guide," pp. A1–A4.

*Primary Examiner*—Margaret R. Wambach
*Attorney, Agent, or Firm*—Duft, Graziano & Forest, P.C.

[57] ABSTRACT

The invention includes a particle sensor with a particle counter. A regenerative blower pulls ambient air into a flow within the particle counter, and a laser illuminates the flow to generate laser radiation indicative of particles within the flow. A detector detects the laser radiation; and particle sensing electronics counts particles within the flow at a preselected volumetric flow rate, e.g., 1 CFM. Preferably, the particle counter includes a plurality of pressure sensors; and a blower speed voltage controller adjusts the speed of the blower according to signals from the pressure sensors to achieve the preselected volumetric flow rate. The regenerative blower permits use of a high efficiency exhaust filter to filter air exhausted from the blower. An airflow path between the particle counter and the regenerative blower preferably has at least one bend between the particle counter and the blower to increase compactness of the system. An aerosol manifold can be connected for fluid communication with an inlet of the particle counter such that the regenerative blower draws air from the manifold at the preselected volumetric flow rate. The manifold samples ambient atmospheric air at a second CFM rate, e.g., 3 CFM, that is greater than the preselected volumetric flow rate. A turbomolecular pump can replace the regenerative blower for high pressure differential particle sensing environments.

17 Claims, 7 Drawing Sheets

AIR PUMP FOR PARTICLE SENSING USING REGENERATIVE FAN, AND ASSOCIATED METHODS

FIELD OF THE INVENTION

The invention relates to particle sensing equipment and methods and, more particularly, to airflow systems that provide precise volumetric airflow to particle sensing equipment.

BACKGROUND OF THE INVENTION

Aerosol optical particle counters of the prior art typically utilize either a mass flow sensor or a pressure sensor, monitoring pressure drop across a restriction, to establish the flow rate within the particle counter. Because these devices are small, inexpensive and readily available, they are extensively used in industry.

Figure 1:
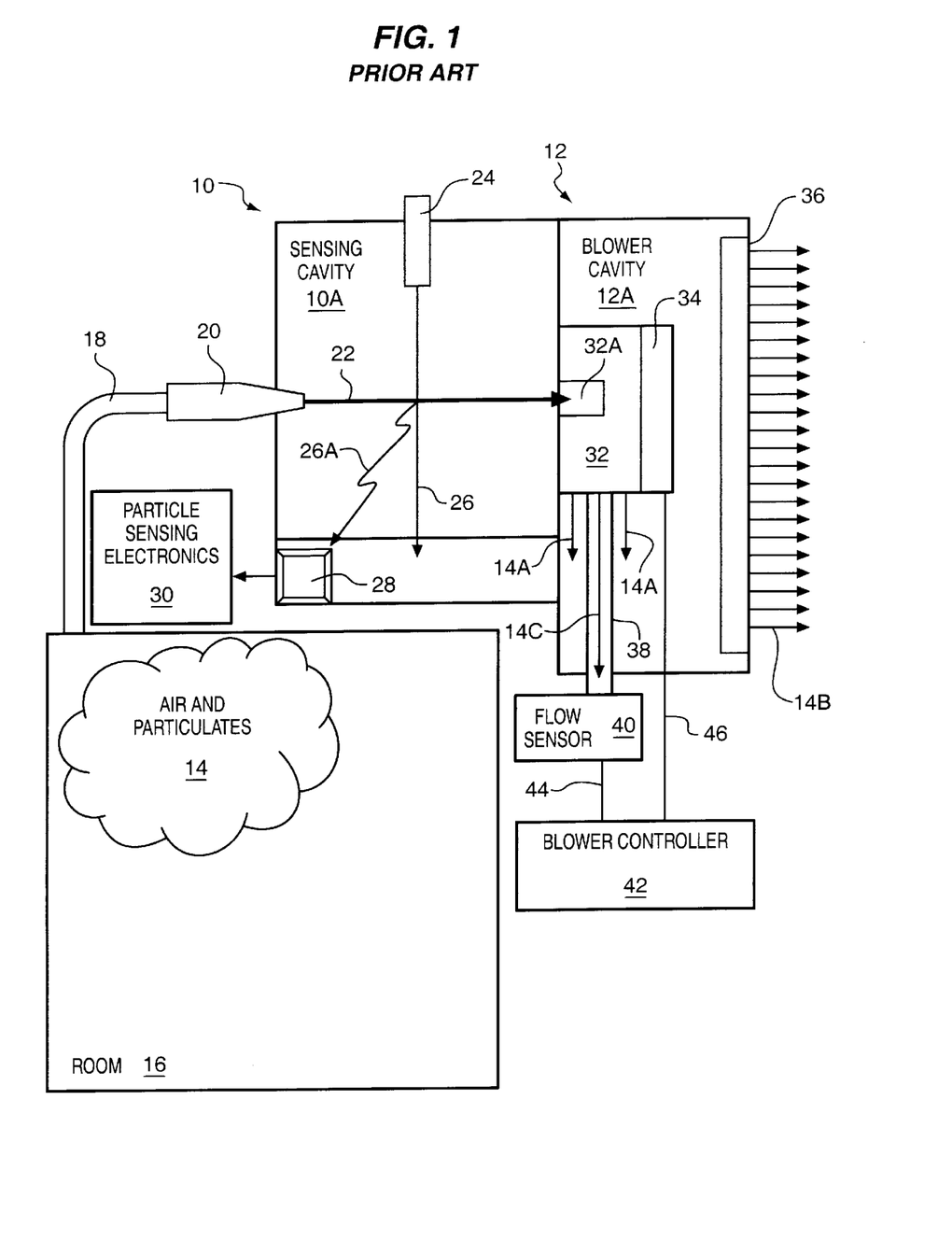

By way of example, the prior art is familiar with particle sensors and associated airflow systems using a centrifugal blower, as described in U.S. Pat. No. 5,515,164. FIG. 1 of the '164 patent illustrates a representative prior art particle sensor 10 and airflow system 12 in this category. Particle sensor 10 has a sensing cavity 10a; and airflow system 12 has a blower cavity 12a. Airflow system 12 draws air from sensing cavity 10a such that air and particulates 14, from room 16, are drawn into sensing cavity 10a through hose 18 and airflow tube 20. Airflow tube 20 is tapered along a single axis such that air and particulates 14 from room 16 are forced into a narrow uniaxial flow 22 within sensing cavity 10a.

Particulates within flow 22 are detected through known techniques. Specifically, laser 24 generates a laser beam 26 that orthogonally illuminates flow 22, creating scattered energy 26a which is functionally dependent upon particulates within flow 22. Detector 28 detects scattered energy 26a; and detector signals from detector 28 are analyzed by particle counting electronics 30 to quantify the number of particles within the flow (for purposes of illustration, detector 28 is shown collecting scattered energy 26a in the same plane as beam 26; while in reality detector 28 typically views scatter 26a orthogonally to both beam 26 and flow 22).

Airflow system 12 includes a centrifugal blower 32 powered by motor 34. Centrifugal blower 32 draws air from within sensing cavity 10a and directly through its center 32a coaligned with flow 22. Exhaust 14a from blower 32 primarily exits blower cavity 12a as exhaust 14b through filter 36; except that a portion of exhaust 14a, denoted as exhaust 14c, is captured by tube 38 and routed to flow sensor 40 to assess the flow rate through blower 32. Blower controller 42 receives electrical signals indicative of flow rate from sensor 40, through signal line 44; and commands motor 34, through signal line 46, to drive blower 32 to a preset speed according to the flow rate. Blower controller 42 thus operates in feedback control of blower 32 via flow rate sensor 40 and motor 34.

It is desirable ill the field of particle sensing to determine the number of particulates for an exact volumetric flow rate (i.e., one cubic foot per minute, or "CFM") as sampled from the ambient environment within room 16. By way of example, particle sensors in "clean rooms," known in the art, assume that contamination levels are measured relative to a volume of air, and not relative to mass, since the mass of a given volume of air can vary by over 20% due to elevational changes alone. Weather fronts induce additional mass-per-volume differentials of up to 3%.

Therefore, one problem in the particle sensor and airflow system 10, 12 of FIG. 1 is that actual volumetric flow rate is calibrated for a given pressure, typically at "sea level," such that particle counting at other locales does not reflect a correct volumetric flow rate. Manual adjustments can be made to compensate for these errors, except that continuous manual adjustment is needed to ensure accuracy over changing environmental (e.g., elevation and barometric pressure) conditions.

Another problem in airflow system 12, FIG. 1, is that centrifugal blower 32 is arranged co-axially about flow 22 because of the physical operation of blower 32: by definition, centrifugal fans draw air through the center of the fan. Accordingly, airflow system 12 has an elongated form along the axis of flow 22, reducing the compactness of airflow system 12 as desired, for example, in hand-held particle sensing applications. Accordingly, to improve compactness, airflow tube 20 is typically made shorter than desired for optimal performance.

Yet another problem with airflow system 12, FIG. 1, is that centrifugal blower 32 is limited in the amount of pressure differential it can handle between sensing cavity 10a and blower cavity 12a, thereby restricting the capability of particle sensing to certain environments. This limitation in operating within certain pressure differentials also limits the amount of filtering which can exist after blower 32 to reduce contamination. More particularly, filter 36 cannot, generally, be a high performance contamination filter because such filters cause additional pressure differential. Prior art airflow systems 12 thus typically utilize a crude filter 36, increasing the likelihood of contamination into sensing cavity 10a or room 14.

It is, accordingly, one object of the invention to provide a particle sensor and airflow system that reduces or eliminates the above-described problems in the prior art Yet another object of the invention is to provide methods of particle sensing with respect to absolute volumetric flow rates regardless of the particle sensor locale. Still another object of the invention is to provide a compact particle sensing system with reduced internal contamination and with reduced external contamination to the environment under measure. These and other objects will be apparent in the description that follows.

SUMMARY OF THE INVENTION

The following patents provide useful background information for the invention ands relating to particle sensors and airflow systems: U.S. Pat. No. 5,467,189; U.S. Pat. No. 5,515,164; U.S. Pat. No. 5,600,438; U.S. Pat. No. 4,571,079; U.S. Pat. No. 4,984,889; U.S. Pat. No. 4,594,715; and U.S. Pat. No. 5,825,487. Each of the aforementioned patents is incorporated herein by reference.

In one aspect, the invention provides a method of controlling volumetric flow rate for a particle counter in ambient atmosphere, including the steps of: pulling ambient air into the particle counter; determining air-flow rate through the particle counter; determining atmospheric pressure; and determining the volumetric flow rate as a function of air-flow rate and atmospheric pressure.

Preferably, the step of determining atmospheric pressure comprises the steps of (a) determining absolute pressure within the particle counter and (b) determining pressure of the ambient atmosphere.

In another aspect, the step of determining air flow rate can include determining differential pressure within the particle counter across a restriction.

The invention of another aspect includes particle sensor. The sensor includes a particle counter and a regenerative blower that pulls ambient air into a flow within the particle counter. A laser illuminates the flow to generate laser radiation indicative of particles within the flow; and a detector detects the laser radiation. Particle sensing electronics evaluate and determine particulates within the flow.

In another aspect, the particle counter includes a plurality of pressure sensors and a blower speed voltage controller. The controller adjusts the speed of the blower according to signals from the pressure sensors such that the flow has a preselected volumetric flow rate. In a preferred aspect, the preselected volumetric flow rate is 1 CFM.

In other aspects, the three pressure sensors include a first pressure sensor for determining flow rate through the particle counter; a second pressure sensor for determining absolute pressure within the particle counter; and a third pressure sensor for determining pressure of the ambient atmosphere surrounding the sensor.

In still another aspect, the sensor includes a high efficiency exhaust filter to filter air exhausted from the blower.

In yet another aspect, the sensor includes an airflow path between the particle counter and the regenerative blower. In this aspect, the airflow path has at least one bends between the particle counter and the blower.

In one aspect, the sensor includes an aerosol manifold connected for fluid communication with an inlet of the particle counter. The regenerative blower draws air from the manifold at the preselected volumetric flow rate; and the aerosol manifold samples ambient atmospheric air at a second CFM rate that is greater than the preselected volumetric flow rate. In one example, the preselected volumetric flow rate is 1 CFM and the second CFM rate is 3 CFM.

In another aspect, the sensor includes a high-flow rate manifold pump. The pump draws air into the aerosol manifold at the second CFM rate and captures exhaust from the particle counter at the preselected volumetric flow rate.

The invention further provides a particle sensing system. The system includes a particle counter, a regenerative blower that pulls ambient air through an airflow tube into a flow within the particle counter, and a plurality of pressure sensors. The system also includes a blower speed voltage controller that adjusts the speed of the blower according to signals from the pressure sensors to achieve a first volumetric flow rate within the particle counter. An aerosol manifold connects in fluid communication with the particle counter to deliver ambient air to the particle counter at the first volumetric flow rate; and a high-flow rate manifold pump captures exhaust from the regenerative blower and the manifold such that the manifold draws ambient atmospheric air within the manifold at a second volumetric flow rate that is greater than the first volumetric flow rate. The manifold permits sampling of multiple locations corresponding to the multiple inlets to the manifold.

The system also preferably includes a high efficiency exhaust filter for filtering air exhausted from the blower.

In still another aspect, the invention provides a particle sensor including a particle counter. A turbomolecular pump pulls ambient air into a flow within the particle counter. A laser illuminates the flow to generate laser radiation indicative of particles within the flow. A detector detects the laser radiation; and particle sensing electronics determine particulates within the flow.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which:

FIG. 1 illustrates a prior art particle sensor and airflow system;

FIG. 2 shows a particle sensing system constructed according to the invention, including a particle sensor, airflow mechanics, and a remote external sampling manifold;

FIG. 2A shows a cut-away top view of part of the manifold of FIG. 2;

FIG. 3 illustrates additional detail of the particle sensor and airflow mechanics of FIG. 1;

FIG. 4 illustrates pressure-sensing techniques used in the system of FIG. 1;

FIGS. 5 and 6 illustrate perspective views of one particle sensor constructed according to the invention; and FIG. 7 schematically illustrates an alternative particle sensor of the invention and utilizing a turbo-molecular pump within the airflow mechanics.

DETAILED DESCRIPTION OF THE DRAWINGS

FIG. 2 illustrates a particle sensing, system 100 constructed according to the invention. Ambient air 101 is captured (i.e., "sampled") by system 100 through one of several inlets 102 that are part of aerosol manifold 104. As shown in FIG. 2A, manifold 104 has a hollow pivot arm 104*a* that rotates 105 within manifold 104 to connect to one inlet 102 that in turn connects to particle sensor 106 through tube 108. Inlet 102, pivot arm 104*a* and tube 108 thus create a path of fluid communication between ambient air 101 and particle sensor 106. Particle sensor 106 measures particulates within air 101 relative to an absolute volumetric flow rate.

In the preferred embodiment, air 101 enters the sampling inlet 102 of system 100 at a rate of 3 CFMs, during operation. Through volumetric flow ratios within pivot arm 104*a* and tube 108, air 101*a* enters particle sensor 106 at a volumetric flow rate of 1 CFM, absolute. Such control is attained through the description that follows.

Air drawn into manifold 104 that is not collected through pivot arm 104*a* and tube 108 is exhausted into high rate manifold exhaust 114, as indicated by exhaust air 107. Similarly, exhaust air 101*b* from particle sensor 106 passes through manifold connector 110 and tubing 112 and into high flow-rate manifold exhaust 114. A high flow-rate manifold pump 116 draws exhaust air 101*b*, 107 from system 100 through manifold exhaust 114. The 3:1 ratio of air 101 entering each inlet 102 relative to air 101*a* entering sensor 106, through pivot arm 104*a*, keeps a continuous flow within sensor 106 and limits cross talk between adjacent inlets 102. More particularly, manifold pump 116 draws the 1 CFM exhaust air 101*b* from regenerative blower 128, FIG. 3, as well as exhaust air 107 originating from manifold sampling inlets 102, each at 3 CFM. If for example manifold 104 has twelve inlets 102, the total flow drawn is 12×3 CFM, plus 1 CFM, or 37 CFM total. Accordingly, manifold pump 116 is sometimes referred to as a "high rate" manifold pump.

As described in more detail below, FIG. 2 illustratively shows that particle sensor 106 includes all airflow sensor 120 to measure differential pressure across a restriction, an atmospheric sensor 122 to measure atmospheric pressure internal to particle counter 106, an absolute pressure sensor 124 to measure absolute pressure of ambient air 101, and a blower speed voltage controller 126 to vary the rotational speed of regenerative blower 128, FIG. 3. Sensors 120, 122, 124 are collectively used by controller 126 to regulate the speed of the regenerative blower 128 within particle sensor 106 to ensure accurate volumetric airflow.

Figure 2:
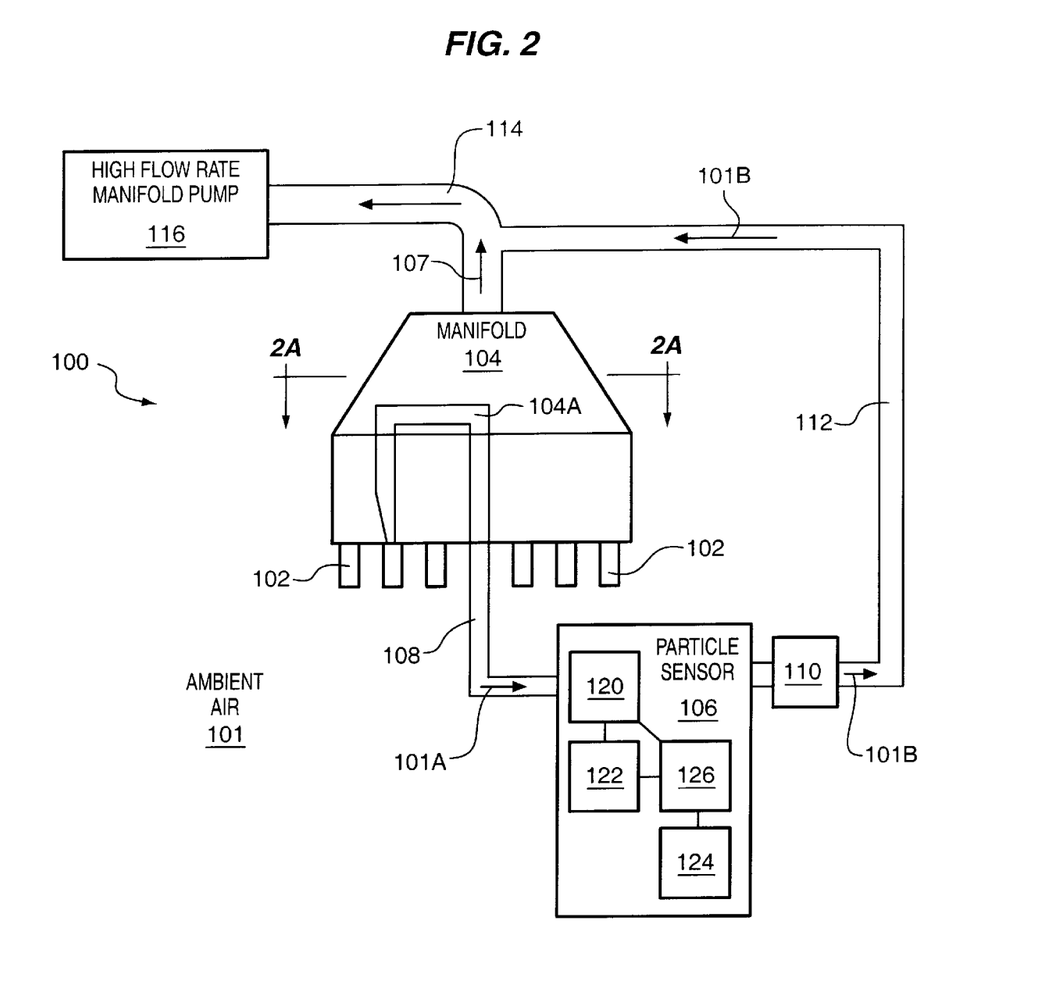
Figure 2A:
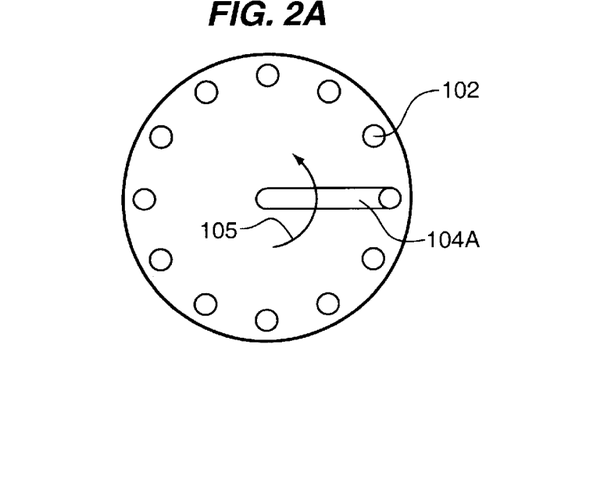
Figure 3:
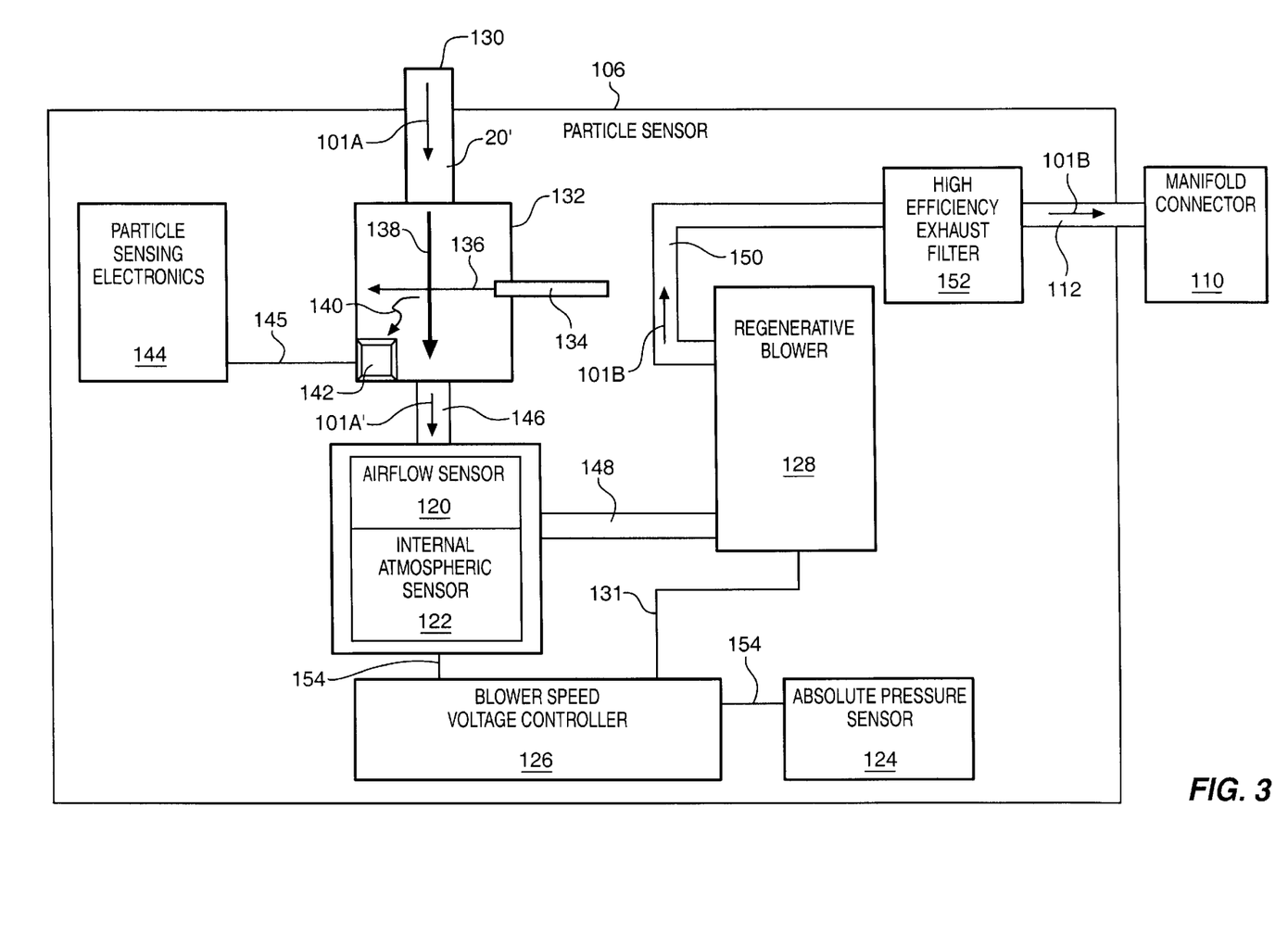

FIG. 3 illustrates further detail of particle sensor 106 and the associated airflow mechanics, including regenerative blower 128, that draw air into, and draw air out of, particle sensor 106. FIG. 3 further illustrates positioning of sensors 120, 122, 124 used by sensor 106 to ensure correct volumetric flow. Regenerative blower 128 draws air 101a into particle sensor 106 through inlet orifice 130, connected for fluid communication with tube 108, FIG. 2, and then into particle counter 172 to evaluate particulates within a flow 138 of air 101a. Particle sensor 106 preferably includes an airflow tube 20', such as airflow tube 20, FIG. 1, to create flow 138. As known in the art, a laser 134 generates a laser beam 136 that illuminates flow 138 such that scattered energy 140, indicative of particles in flow 138, is detected by detector 142. Particle sensing electronics 144 evaluate signals from detector 142, through signal line 145, to quantify these particulates for the selected volumetric flow rate, e.g., 1 CFM.

Regenerative blower 128 further draws air 101a' from counter 132 through connecting tube 146 anld through airflow and internal atmospheric sensors 120, 122. Airflow sensor 120 measures airflow of air 101a' across a restriction, described in connection with FIG. 4, and internal atmospheric sensor 122 measures pressure within sensor 106. Blower 128 draws air 101a' through connecting tube 148 and exhausts air 101b through connecting tube 150, high efficiency exhaust filter 152, tubing 112 and manifold connector 110. The only exit of exhaust from particle sensor 106 is through filter 152, which cleans exhausted air 101b to reduce contamination within system 100, FIG. 2.

Atmospheric pressure sensor 124 provides absolute pressure of ambient air 101 entering system 100. Blower speed voltage controller 126 receives signals from sensors 120, 122, 124, via signal lines 154, and regulates the DC voltage, and thus the speed, of regenerative blower 128, through signal line 131, to control the volumetric flow rate of air 101a entering particle sensor 106.

Figure 4:
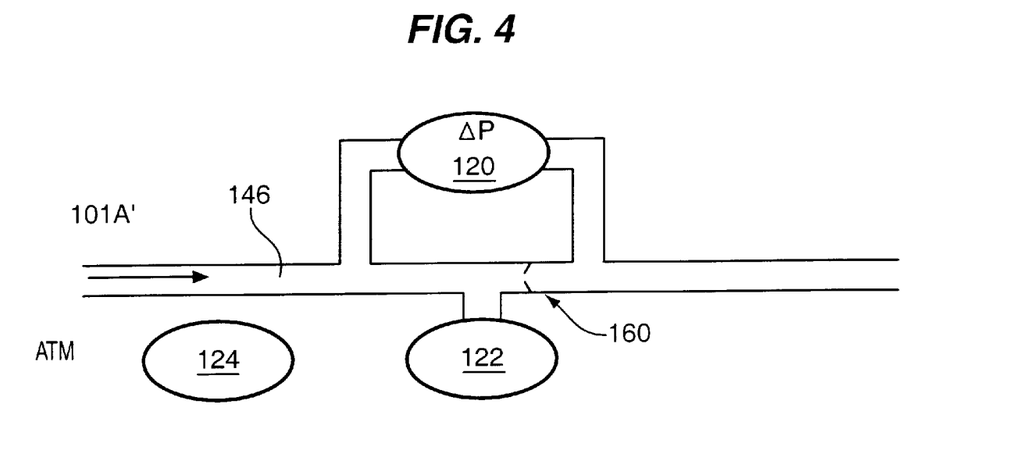

FIG. 4 illustrates the principles of pressure sensing within sensor 106 to attain accurate volumetric flow rate within sensor 106. The flow rate (molecules/second) of air 101a' in sample tube 146 is measured by airflow sensor 120 across restricting orifice 160. Pressure sensor 122 measures the density of air inside sample tube 146. To attain the number of particulates at a desired volumetric flow, volumetric flow is determined by the flow rate and the atmospheric pressure as provided by airflow sensor 120 and pressure sensor 122, respectively. Pressure sensor 122 can be located elsewhere within system 100; except that a more accurate volumetric flow rate can be determined with pressure sensor 122 locally in sensor 106.

More particularly, variable speed regenerative blower 128 FIG. 3, is used as the air-moving device within sensor 106. Differential airflow pressure sensor 120 is used in tandem with restricting orifice 160 to measure the differential pressure drop across orifice 160 caused by air-flow through orifice 160. Pressure sensor 122 is used to measure the absolute air pressure directly upstream of restricting orifice 160. Absolute pressure sensor 124 is used to measure the absolute air pressure of the ambient air 101. Blower controller 126 interprets the information provided by pressure sensors 120, 122, 124 and derives an output signal, on signal line 131 that controls the speed of regenerative blower 128. System 100 thus provides a closed loop feedback control of blower 128.

System 100, FIG. 2, preferably provides an accurate 1 CFM volumetric flow rate as sampled from the ambient environment (i.e., the source of air 101). System 100 is intended to be used at elevations ranging approximately from sea level to 10,000 feet. System 100 is also preferably designed to be used in conjunction with aerosol manifold 104 that will expose all components of system 100, with the exception of pressure sensor 124, to approximately sixty inches of water vacuum in respect to the ambient environment. The differential pressure signal, $\Delta P$, generated by sensor 120 is proportional to the flow rate through particle sensor 106; however the Bernoulli equation requires that the air density at sensor 120 be known in order to derive the actual volumetric flow rate. Pressure sensor 122 is used to measure this air density.

Pressure drops in the upstream flow of pressure sensor 122 causes the air density at its location to be slightly different than at the ambient environment of air 101. When connected to aerosol manifold 104, this air density is significantly different than at ambient. Therefore the pressure ratio (pressure from pressure sensor 122 divided pressure from pressure sensor 124) is interpreted in order to maintain the required volumetric flow rate at airflow sensor 120, corresponding to 1 CFM volumetric flow rate drawn from ambient environment.

System 100 thus produces an accurate 1 CFM volumetric flow rate at the current ambient environment conditions as compensated for varying air density, due to site elevation, and local air pressure changes, due to environmental conditions.

The following equations are useful in determining the volumetric flow rate:
Ideal Gas Law $$\rho = PM/RT$$

where $\rho$=Density (kg/m$^3$)
P=Pressure (kPa)
M=Molar mass of air (28.97 kg/kmol)
R=Universal Gas Constant (8.314 kJ/kmol·K)
T=Temperature (° K)
Bernoulli equation $$Q = k \cdot [(2 \cdot \Delta P)/\rho]^{1/2}$$

where Q=Volumetric Flow
k=empirically determined constant
$\Delta P$=Differential pressure
$\rho$=Density
Simplified equation for volumetric flow, Q, within sensor 106:

$$Q = k \cdot [(P_{APSO} \cdot P_{DPS})^{1/2} \div P_{APSE}]$$

where Q=Ambient Volumetric Flow
k=empirically determined constant
$P_{APSO}$=Pressure of pressure sensor 124
$P_{DPS}$=Differential pressure of airflow sensor 120
$P_{APSE}$=Pressure of pressure sensor 122
With regard to FIG. 2, it should be noted that particle sensor 106 can operate without use of, or connection to, manifold 104, tubing 108, 112, high flow rate manifold pump 116 and manifold exhaust 114. However, once connected to the foregoing, the pressure within manifold 104 is preferably lower than ambient, at approximately sixty inches of water; hence the purpose for pressure sensor 124 the prior art does not provide for the advantages associated with operating in closed loop with a manifolds 104 at 60" of $H_2O$. Without manifold 104, the pressures defined by sensors 122, 124 are approximately the same.

Figure 5:
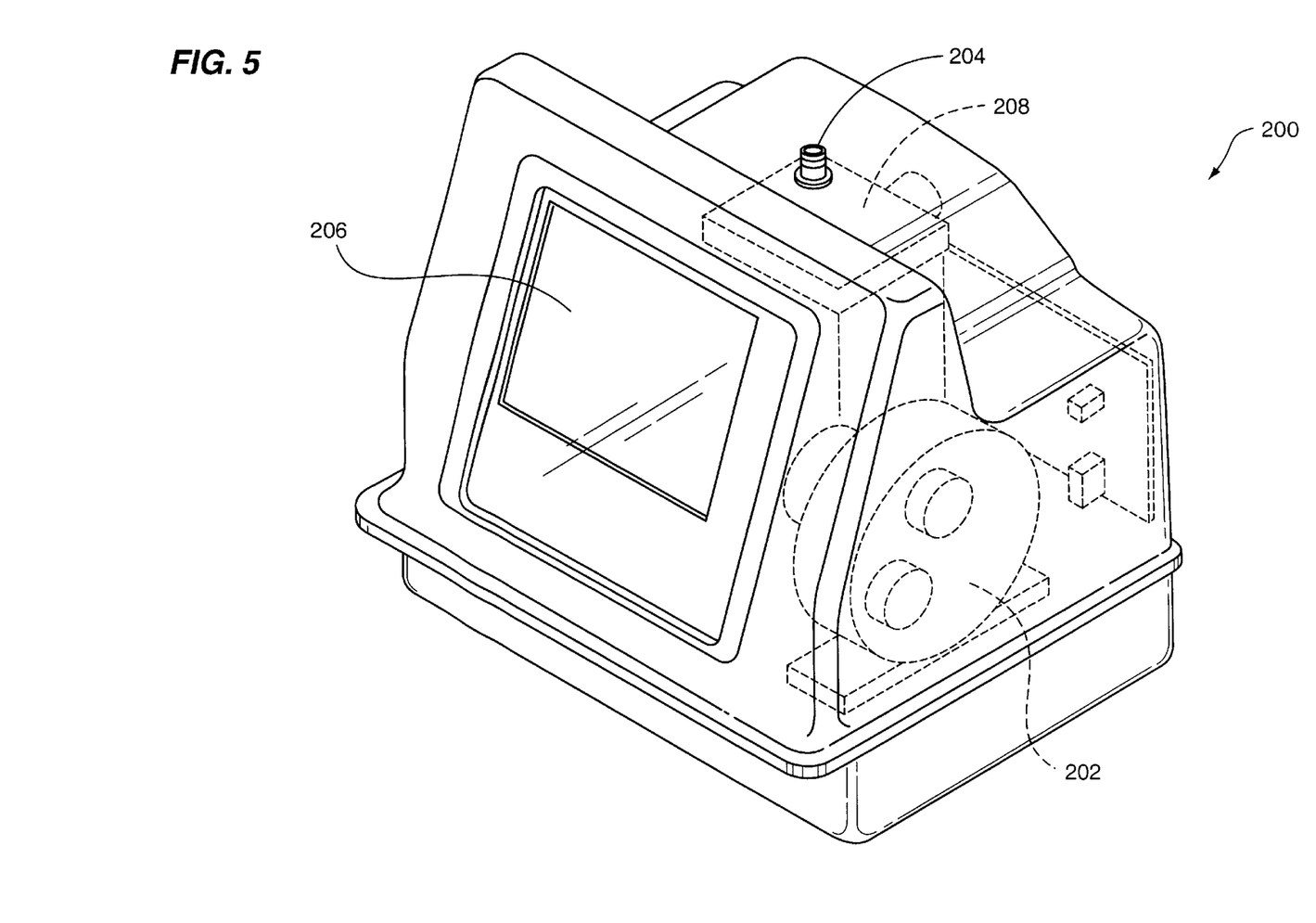

FIG. 5 illustrates a perspective view of one particle hand-held particle sensor 200 constructed according to the invention. As in FIG. 2, a regenerative blower 202 provides the push and pull of airflow within sensor 200. Internal electronics (e.g., similar to electronics 144, FIG. 3) and particle counter 208 (similar to counter 106, FIG. 2) determine particulates within a flow of ambient air entering inlet aperture 204; and a color LCD display 206 displays results to users of sensor 200. Internal operation, pressure sensing and airflow within sensor 200 operates as described above with respect to FIGS. 2–4.

Figure 6:
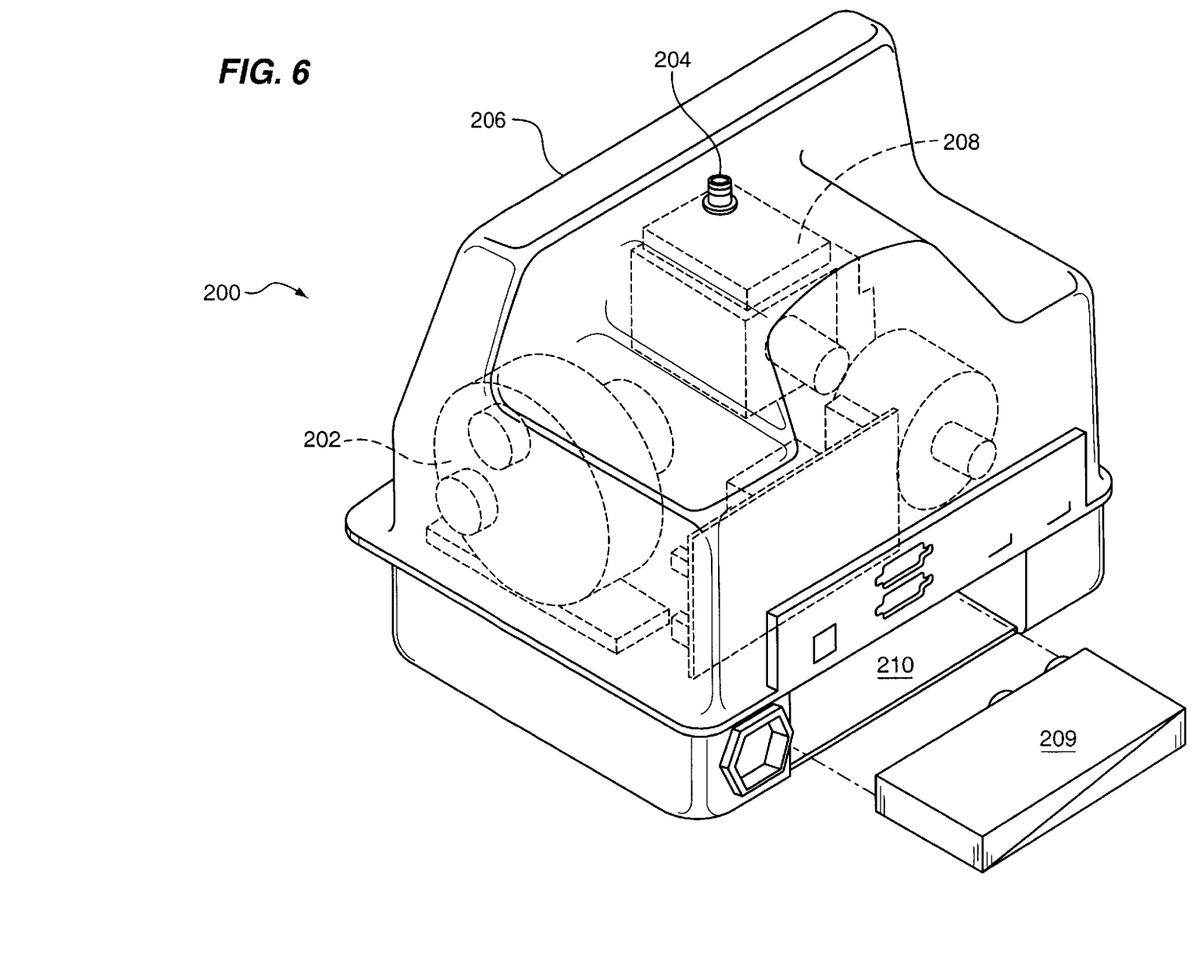

FIG. 6 shows an alternative perspective view of sensor 200; and additionally illustrates a removable battery pack 209 used to power blower 202, the motor controller (e.g., similar to motor controller 126, FIG. 3), and other parts requiring power within sensor 202. Battery pack 209 slides in and out of battery bay 210 selectively.

FIGS. 2–3, 5–6 illustrate the compactness of a particle sensor constructed according to the invention. The regenerative blower provides for convenient positioning within the sensor, and the non-linear arrangement of inlet tubes and tubing to the blower provides additional compactness. The prior art of FIG. 1, on the other hand, requires co-alignment between the airflow tube and the centrifugal blower along a common air-flow axis, limiting the compactness of the resulting particle sensor without shortening of an optimal airflow tube. The system of the invention, on the other hand, desirably permits extension of the inlet tube into the particle counter. Regenerative fans also require fewer RPMs to pull the same amount of air volume through such fans, as compared to centrifugal fans; and are thus quieter in use.

Figure 7:
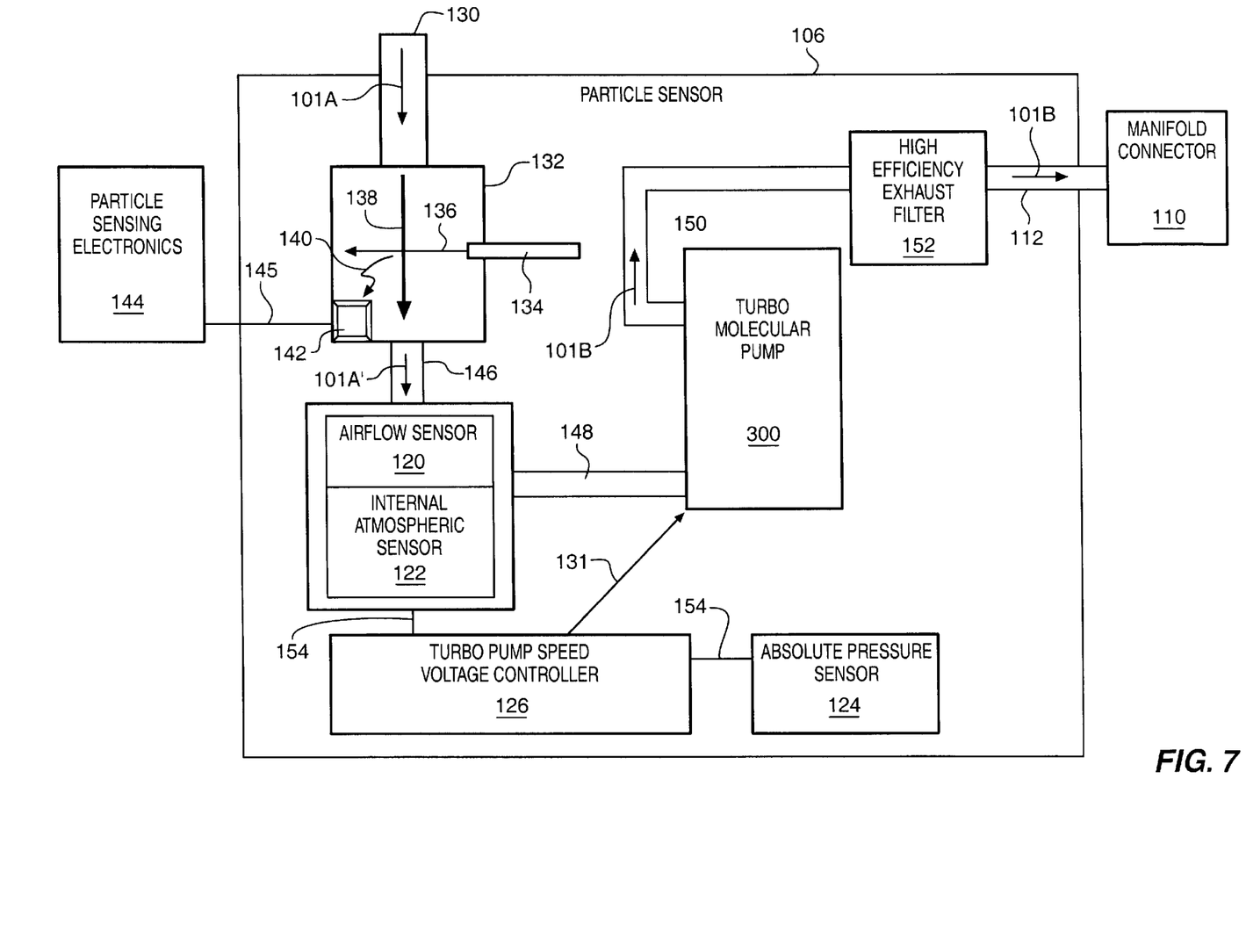

FIG. 7 illustrates an alternative particle sensor 106', similar to sensor 106, FIG. 3, except for the use of a turbomolecular pump 300 and turbopump controller 302 in place of regenerative blower 128 and controller 126, respectively; like numbers having like function relative to earlier descriptions. Turbo pumps have advantages over other pumps particularly in the area of vacuum displacement: turbo pumps can draw a much higher vacuum, and create a much higher airflow, than other conventional pumps. The following patents provide useful background information for turbo pump operations and are thus incorporated herein by reference: U.S. Pat. No. 3,832,084; U.S. Pat. No. 3,969, 042; U.S. Pat. No. 4,929,151; U.S. Pat. No. 4,893,985; U.S. Pat. No. 4,764,034; U.S. Pat. No. 4,734,018; U.S. Pat. No. 3,753,623; U.S. Pat. No. 3,947,193; U.S. Pat. No. 5,451,147; and U.S. Pat. No. 4,180,370.

The invention thus attains the objects set forth above, among those apparent from the preceding description. Since certain changes may be made in the above methods and systems without departing from the scope of the invention, it is intended that all matter contained in the above description or shown in the accompanying drawing be interpreted as illustrative and not in a limiting sense. For example, those skilled in the art should appreciate that several regenerative blowers can be used with the invention, such as the MINISPIRAL™ regenerative blowers (e.g., MDC part number SE12V21-037433) by the Rotron Technical Motor Division of AMETEK®.

It is also to be understood that the following claims are to cover all generic and specific features of the invention described herein, and all statements of the scope of the invention which, as a matter of language, might be said to fall there between.

Having described the invention, what is claimed is:

1. A method of controlling volumetric flow rate for a particle counter in ambient atmosphere, comprising the steps of:

pulling ambient air into the particle counter;

determining air-flow rate through the particle counter;

determining atmospheric pressure; and determining the volumetric flow rate as a function of air-flow rate and atmospheric pressure.

2. A method of claim 1, wherein the step of determining atmospheric pressure comprises the steps of determining absolute pressure within the particle counter and determining pressure of the ambient atmosphere.

3. A method of claim 2, wherein the step of determining volumetric flow rate comprises determining volumetric flow rate as Q in the following relationship:

$$Q = k \cdot [(P_{APSO} \cdot P_{DPS})^{1/2} P_{APSE}],$$

where k is an empirically determined constant, $P_{APSO}$ is the absolute pressure within the particle counter, $P_{DPS}$ is differential pressure, proportionate to flow rate, and $P_{APSE}$ is the ambient atmospheric pressure.

4. A method of claim 3, wherein the step of determining volumetric flow rate comprises utilizing the following relationship in the evaluation of Q:

$$Q = k \cdot [(2 \cdot \Delta P)/\rho]^{1/2}$$

where

ΔP is differential pressure in the particle counter across a restriction,

ρ is PM/RT ($kg/m^3$),

P is pressure (kPa),

M is molar mass of air (28.97 kg/kmol),

R is Universal Gas Constant (8.314 kJ/kmol·K), and

T is temperature (° K).

5. A method of claim 1, wherein the step of determining air flow rate comprises determining differential pressure within the particle counter across a restriction.

6. A particle sensor, comprising: a particle counter, a regenerative blower for pulling ambient air into a flow within the particle counter, a laser for illuminating the flow to generate laser radiation indicative of particles within the flow, a detector for detecting the laser radiation, and particle sensing electronics for determining particulates within the flow.

7. A particle sensor of claim 6, wherein the particle counter comprises a plurality of pressure sensors, further comprising a blower speed voltage controller for adjusting the speed of the blower according to signals from the pressure sensors, wherein the flow has a preselected volumetric flow rate.

8. A particle sensor of claim 7, wherein the preselected volumetric flow rate is 1CFM.

9. A particle sensor of claim 7, wherein the plurality pressure sensors comprise a first pressure sensor for determining flow rate through the particle counter; a second pressure sensor for determining absolute pressure within the particle counter; and a third pressure sensor for determining pressure of the ambient atmosphere surrounding the sensor.

10. A particle sensor of claim 6, further comprising a high efficiency exhaust filter for filtering air exhausted from the blower.

11. A particle sensor of claim 6, further comprising an airflow path between the particle counter and the regenerative blower, the airflow path having at least one bend between the particle counter and the blower.

12. A particle sensor of claim 6, further comprising an aerosol manifold connected for fluid communication with an inlet of the particle counter, the regenerative blower drawing air from the manifold at the preselected volumetric flow rate, the aerosol manifold sampling ambient atmospheric air at a second CFM rate that is greater than the preselected volumetric flow rate.

13. A particle sensor of claim 12, wherein preselected volumetric flow rate is 1 CFM and the second CFM rate is 3 CFM.

14. A particle sensor of claim 12, further comprising a high-flow rate manifold pump connected to draw air into the aerosol manifold at the second CFM rate and to capture exhaust from the particle counter at the preselected volumetric flow rate.

15. A particle sensing system, comprising a particle counter, a regenerative blower for pulling ambient air through an airflow tube into a flow within the particle counter, a plurality of pressure sensors, a blower speed voltage controller for adjusting the speed of the blower according to signals from the pressure sensors to achieve a first volumetric flow rate within the particle counter, an aerosol manifold connected in fluid communication with the particle counter to deliver ambient air to the particle counter at the first volumetric flow rate, a high-flow rate manifold pump connected to capture exhaust from the regenerative blower and the manifold such that the manifold draws ambient atmospheric air within the manifold at a second volumetric flow rate that is greater than the first volumetric flow rate.

16. A particle sensing system of claim 15, further comprising a high efficiency exhaust filter for filtering air exhausted from the blower, the exhaust filter being in closed loop fluid communication with exhaust from the manifold.

17. A particle sensor, comprising: a particle counter, a turbomolecular pump for pulling ambient air into a flow within the particle counter, a laser for illuminating the flow to generate laser radiation indicative of particles within the flow, a detector for detecting the laser radiation, and particle sensing electronics for determining particulates within the flow.

* * * * *